(12) United States Patent
Akyuz et al.

(10) Patent No.: US 8,177,796 B2
(45) Date of Patent: May 15, 2012

(54) SUTURE PASSING APPARATUS AND METHOD

(75) Inventors: Ephraim Akyuz, Providence, UT (US); Andrew R. Fauth, River Heights, UT (US); Joseph A. Fritz, Largo, FL (US); Jason Glad, Lewiston, UT (US); Daniel Justin, Logan, UT (US); Douglas M. Lorang, North Logan, UT (US); Matthew C. Summitt, Palm Harbor, FL (US); M. Mary Sinnott, Logan, UT (US); Daniel J. Triplett, Providence, UT (US)

(73) Assignee: Linvatec Corporation, Largo, FL (US)

( * ) Notice: Subject to any disclaimer, the term of this patent is extended or adjusted under 35 U.S.C. 154(b) by 282 days.

(21) Appl. No.: 12/728,768

(22) Filed: Mar. 22, 2010

(65) Prior Publication Data

US 2010/0241142 A1 Sep. 23, 2010

Related U.S. Application Data

(60) Provisional application No. 61/162,601, filed on Mar. 23, 2009, provisional application No. 61/261,551, filed on Nov. 16, 2009, provisional application No. 61/261,658, filed on Nov. 16, 2009.

(51) Int. Cl.
*A61B 17/04* (2006.01)

(52) U.S. Cl. .......................................... 606/144; 606/148

(58) Field of Classification Search .................. 606/139, 606/144, 145, 148
See application file for complete search history.

(56) References Cited

U.S. PATENT DOCUMENTS

| 349,791 | A | 9/1886 | Gibboney |
|---|---|---|---|
| 1,037,864 | A | 9/1912 | Carlson |
| 1,449,087 | A | 3/1923 | Hugbee |
| 1,464,832 | A | 8/1923 | Richardson |
| 1,635,066 | A | 7/1927 | Wells |
| 1,641,077 | A | 8/1927 | Fouguet |
| 1,656,467 | A | 1/1928 | Blake |
| 1,815,725 | A | 7/1931 | Pilling |
| 1,856,721 | A | 5/1932 | Nagelman |
| 2,213,830 | A | 9/1940 | Anestasi |
| 2,286,578 | A | 6/1942 | Sauter |
| 2,738,790 | A | 3/1956 | Todt |
| 2,959,172 | A | 11/1960 | Held |
| 3,090,386 | A | 5/1963 | Babcock |
| 3,349,772 | A | 10/1967 | Rugg |
| 3,372,477 | A | 3/1968 | Clements |
| 3,470,875 | A | 10/1969 | Johnson |

(Continued)

FOREIGN PATENT DOCUMENTS

EP 315371 10/1989

(Continued)

*Primary Examiner* — Julian Woo

(57) ABSTRACT

An endoscopic surgical instrument for passing a suture through tissue includes a first jaw member, a needle, and a capture feature actuable to grip and retain the suture after the suture has been passed through a tissue body. An actuation mechanism can both move the needle between retracted and extended positions, and move the capture feature between open and closed configurations, via a single actuation. The capture feature may be a trap door which is axially translatable relative to the first jaw member to overlap a portion of the first jaw member and trap a portion of the suture between the trap door and the overlapped portion. The first jaw member may be movable relative to a second jaw member to grasp a tissue body. The instrument can grasp a tissue body, pass the suture through the tissue, capture and retain the suture without being repositioned relative to the tissue.

30 Claims, 13 Drawing Sheets

U.S. PATENT DOCUMENTS

| | | |
|---|---|---|
| 3,638,654 A | 2/1972 | Akuba |
| 3,807,407 A | 4/1974 | Schweizer |
| 3,842,840 A | 10/1974 | Schweizer |
| 3,946,740 A | 3/1976 | Bassett |
| 4,161,951 A | 7/1979 | Scanlan |
| 4,164,225 A | 8/1979 | Johnson |
| 4,224,947 A | 9/1980 | Fukuda |
| 4,312,337 A | 1/1982 | Donohue |
| 4,373,530 A | 2/1983 | Kilejian |
| 4,440,171 A | 4/1984 | Nomoto |
| 4,484,580 A | 11/1984 | Nomoto |
| 4,496,090 A | 1/1985 | Crevier |
| 4,557,265 A | 12/1985 | Anderson |
| 4,596,249 A | 6/1986 | Freda |
| 4,621,640 A | 11/1986 | Mulhollan |
| 4,779,616 A | 10/1988 | Johnson |
| 4,890,615 A | 1/1990 | Caspari |
| 4,923,461 A | 5/1990 | Caspari |
| 4,935,027 A | 6/1990 | Yoone |
| 4,957,498 A | 9/1990 | Caspari |
| 5,059,201 A | 10/1991 | Asnis |
| 5,147,373 A | 9/1992 | Ferzli |
| 5,149,329 A | 9/1992 | Richardson |
| 5,152,769 A | 10/1992 | Baber |
| 5,181,919 A | 1/1993 | Bergman |
| 5,222,508 A | 6/1993 | Contarini |
| 5,222,962 A | 6/1993 | Burkhart |
| 5,222,977 A | 6/1993 | Esser |
| 5,234,443 A | 8/1993 | Phan |
| 5,254,126 A | 10/1993 | Filipi |
| 5,275,613 A | 1/1994 | Haber |
| 5,279,311 A | 1/1994 | Snyder |
| 5,282,800 A | 2/1994 | Foshee |
| 5,282,806 A | 2/1994 | Haber |
| 5,282,809 A | 2/1994 | Kammerer |
| 5,312,422 A | 5/1994 | Trott |
| 5,318,579 A | 6/1994 | Chow |
| 5,320,632 A | 6/1994 | Heidmueller |
| 5,352,237 A | 10/1994 | Rodak |
| 5,364,408 A | 11/1994 | Gordon |
| 5,364,409 A | 11/1994 | Kuwabara |
| 5,382,258 A | 1/1995 | Chow |
| 5,387,221 A | 2/1995 | Bisgaard |
| 5,389,103 A | 2/1995 | Melzer |
| 5,397,325 A | 3/1995 | Della |
| 5,403,328 A | 4/1995 | Shallman |
| 5,431,666 A | 7/1995 | Sauer |
| 5,437,680 A | 8/1995 | Yoon |
| 5,439,467 A | 8/1995 | Benderev |
| 5,454,823 A | 10/1995 | Richardson |
| 5,462,562 A | 10/1995 | Elkus |
| 5,474,565 A | 12/1995 | Trott |
| 5,480,406 A | 1/1996 | Nolan |
| 5,496,335 A | 3/1996 | Thomason |
| 5,499,991 A | 3/1996 | Garman |
| D368,776 S | 4/1996 | Toy |
| 5,522,820 A | 6/1996 | Caspari |
| 5,540,704 A | 7/1996 | Gordon |
| 5,544,664 A | 8/1996 | Benderev |
| 5,562,686 A | 10/1996 | Sauer |
| 5,569,269 A | 10/1996 | Hart |
| 5,571,090 A | 11/1996 | Sherts |
| 5,573,542 A | 11/1996 | Stevens |
| 5,593,421 A | 1/1997 | Bauer |
| 5,613,977 A | 3/1997 | Weber |
| 5,632,751 A | 5/1997 | Piraka |
| 5,643,292 A | 7/1997 | Hart |
| 5,645,552 A | 7/1997 | Sherts |
| 5,653,716 A | 8/1997 | Malo |
| 5,662,663 A | 9/1997 | Shallman |
| 5,665,096 A | 9/1997 | Yoon |
| 5,674,229 A | 10/1997 | Tovey |
| 5,674,230 A | 10/1997 | Tovey |
| 5,690,652 A | 11/1997 | Wurster |
| 5,690,653 A | 11/1997 | Richardson |
| 5,700,272 A | 12/1997 | Gordon |
| 5,707,379 A | 1/1998 | Fleenor |
| 5,713,908 A | 2/1998 | Jameel |
| 5,728,107 A | 3/1998 | Zlock |
| 5,728,112 A | 3/1998 | Yoon |
| 5,728,113 A | 3/1998 | Sherts |
| 5,730,747 A | 3/1998 | Ek |
| 5,759,188 A | 6/1998 | Yoon |
| 5,776,150 A | 7/1998 | Nolan |
| 5,797,927 A | 8/1998 | Yoon |
| 5,824,009 A | 10/1998 | Fukuda |
| 5,833,697 A | 11/1998 | Ludwick |
| 5,843,099 A | 12/1998 | Nichols |
| 5,843,126 A | 12/1998 | Jameel |
| 5,871,488 A | 2/1999 | Tovey |
| 5,895,393 A | 4/1999 | Pagedas |
| 5,895,395 A | 4/1999 | Yeung |
| 5,904,692 A | 5/1999 | Steckel |
| 5,908,428 A | 6/1999 | Scirica |
| 5,910,148 A | 6/1999 | Reimels |
| 5,928,268 A | 7/1999 | Butwell |
| 5,935,149 A | 8/1999 | Ek |
| 5,938,668 A | 8/1999 | Scirica |
| 5,947,982 A | 9/1999 | Duran |
| 5,954,731 A | 9/1999 | Yoon |
| 5,954,733 A | 9/1999 | Yoon |
| 5,957,937 A | 9/1999 | Yoon |
| 5,961,530 A | 10/1999 | Moore |
| 5,980,538 A | 11/1999 | Fuchs |
| 5,984,932 A | 11/1999 | Yoon |
| 5,993,466 A | 11/1999 | Yoon |
| 5,993,467 A | 11/1999 | Yoon |
| 6,017,358 A | 1/2000 | Yoon |
| 6,022,360 A | 2/2000 | Reimels |
| 6,036,699 A | 3/2000 | Andreas |
| 6,051,006 A | 4/2000 | Shluzas |
| 6,059,800 A | 5/2000 | Hart |
| 6,063,096 A | 5/2000 | Boebel |
| 6,080,180 A | 6/2000 | Yoon |
| 6,126,665 A | 10/2000 | Yoon |
| 6,126,666 A | 10/2000 | Trapp |
| 6,132,439 A | 10/2000 | Kontos |
| 6,143,005 A | 11/2000 | Yoon |
| 6,159,224 A | 12/2000 | Yoon |
| 6,171,317 B1 | 1/2001 | Jackson |
| 6,183,484 B1 | 2/2001 | Matsutani |
| 6,200,329 B1 | 3/2001 | Fung |
| 6,214,028 B1 | 4/2001 | Yoon |
| 6,217,592 B1 | 4/2001 | Freda |
| 6,254,620 B1 | 7/2001 | Koh |
| 6,261,307 B1 | 7/2001 | Yoon |
| 6,322,570 B1 | 11/2001 | Matsutani |
| 6,332,889 B1 | 12/2001 | Sancoff |
| 6,443,963 B1 | 9/2002 | Baldwin |
| 6,454,778 B2 | 9/2002 | Kotenbach |
| 6,511,487 B1 | 1/2003 | Oren |
| 6,511,489 B2 | 1/2003 | Field |
| 6,527,785 B2 | 3/2003 | Sancoff |
| 6,533,795 B1 | 3/2003 | Tran |
| 6,551,329 B1 | 4/2003 | Kortenbach |
| 6,551,330 B1 | 4/2003 | Bain |
| 6,592,559 B1 | 7/2003 | Pakter |
| 6,605,096 B1 | 8/2003 | Ritchart |
| 6,616,674 B2 | 9/2003 | Schmieding |
| 6,638,283 B2 | 10/2003 | Thal |
| 6,638,286 B1 | 10/2003 | Burbank |
| 6,663,639 B1 | 12/2003 | Laufer |
| 6,663,643 B2 | 12/2003 | Field |
| 6,723,107 B1 | 4/2004 | Skiba |
| 6,767,352 B2 | 7/2004 | Field |
| 6,770,084 B1 | 8/2004 | Bain |
| 6,773,441 B1 | 8/2004 | Laufer |
| 6,786,913 B1 | 9/2004 | Sancoff |
| 6,821,285 B2 | 11/2004 | Laufer |
| 6,835,200 B2 | 12/2004 | Laufer |
| 6,843,796 B2 | 1/2005 | Harari |
| 6,893,448 B2 | 5/2005 | O'Quinn |
| 6,896,686 B2 | 5/2005 | Weber |
| 6,936,054 B2 | 8/2005 | Chu |
| 6,955,643 B2 | 10/2005 | Gellman |
| 6,984,237 B2 | 1/2006 | Hatch |
| 6,991,636 B2 | 1/2006 | Rose |

| Patent No. | Date | Inventor |
|---|---|---|
| 6,997,932 B2 | 2/2006 | Dreyfuss |
| 7,008,375 B2 | 3/2006 | Weisel |
| 7,011,668 B2 | 3/2006 | Sancoff |
| 7,033,379 B2 | 4/2006 | Peterson |
| 7,037,315 B2 | 5/2006 | Sancoff |
| 7,048,748 B1 | 5/2006 | Ustuner |
| 7,048,749 B2 | 5/2006 | Kortenbach |
| D523,554 S | 6/2006 | Weisel |
| D529,173 S | 9/2006 | Weisel |
| 7,108,710 B2 | 9/2006 | Anderson |
| 7,112,208 B2 | 9/2006 | Morris |
| D530,421 S | 10/2006 | Topper |
| 7,118,583 B2 | 10/2006 | O'Quinn |
| 7,122,040 B2 | 10/2006 | Hill |
| 7,131,978 B2 | 11/2006 | Sancoff |
| 7,131,979 B2 | 11/2006 | DiCarlo |
| 7,131,980 B1 | 11/2006 | Field |
| 7,153,312 B1 | 12/2006 | Torrie |
| 7,156,857 B2 | 1/2007 | Pasricha |
| 7,166,116 B2 | 1/2007 | Lizardi |
| 7,220,266 B2 | 5/2007 | Gambale |
| 7,232,447 B2 | 6/2007 | Gellman |
| 7,264,623 B2 | 9/2007 | Harris |
| 7,306,613 B2 | 12/2007 | Kawashima |
| 7,316,694 B2 | 1/2008 | Reinitz |
| 7,326,213 B2 | 2/2008 | Benderev |
| 7,364,541 B2 | 4/2008 | Chu |
| 7,377,926 B2 | 5/2008 | Topper |
| 7,377,927 B2 | 5/2008 | Burdulis |
| 7,377,933 B2 | 5/2008 | Martin |
| 7,381,212 B2 | 6/2008 | Topper |
| 7,390,329 B2 | 6/2008 | Westra |
| 7,399,304 B2 | 7/2008 | Gambale |
| 7,416,556 B2 | 8/2008 | Jackson |
| D578,649 S | 10/2008 | Jordan |
| 7,442,198 B2 | 10/2008 | Gelman |
| 7,445,626 B2 | 11/2008 | Songer |
| 2001/0031984 A1 | 10/2001 | Hart |
| 2002/0147456 A1 | 10/2002 | Diduch |
| 2003/0233106 A1 | 12/2003 | Dreyfuss |
| 2004/0010273 A1 | 1/2004 | Diduch |
| 2004/0167548 A1 | 8/2004 | Bonutti |
| 2004/0176802 A1 | 9/2004 | Skiba |
| 2004/0249393 A1 | 12/2004 | Weisel |
| 2004/0249394 A1 | 12/2004 | Morris et al. |
| 2004/0254605 A1 | 12/2004 | DiFrancesco |
| 2005/0234479 A1 | 10/2005 | Hatch |
| 2005/0288690 A1 | 12/2005 | Bourque |
| 2006/0069399 A1 | 3/2006 | Weisel |
| 2006/0074407 A1 | 4/2006 | Padget |
| 2007/0100357 A1 | 5/2007 | Chan |
| 2008/0027468 A1 | 1/2008 | Fenton |
| 2009/0012538 A1 | 1/2009 | Saliman |

FOREIGN PATENT DOCUMENTS

| | | |
|---|---|---|
| EP | 567130 | 10/1993 |
| EP | 571057 | 11/1993 |
| EP | 778004 | 6/1997 |
| EP | 812572 | 6/1997 |
| GB | 2211779 | 7/1989 |
| WO | WO9212674 | 8/1992 |
| WO | WO9313714 | 7/1993 |
| WO | WO9324060 | 12/1993 |
| WO | WO9405217 | 3/1994 |
| WO | WO9414381 | 7/1994 |
| WO | WO9415537 | 7/1994 |
| WO | WO9502998 | 2/1995 |
| WO | WO9522932 | 8/1995 |
| WO | WO9639948 | 12/1996 |
| WO | WO9903402 A | 1/1999 |
| WO | WO0061013 | 10/2000 |
| WO | WO03028532 | 4/2003 |
| WO | WO2006026520 | 3/2006 |
| WO | WO2007146842 | 12/2007 |
| WO | WO2008013864 | 1/2008 |

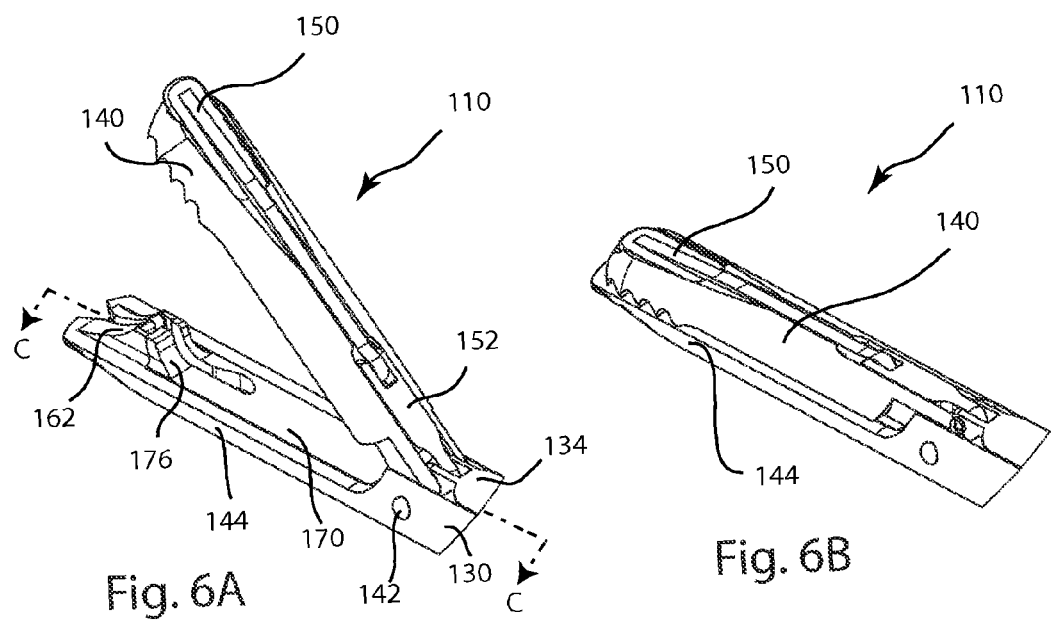
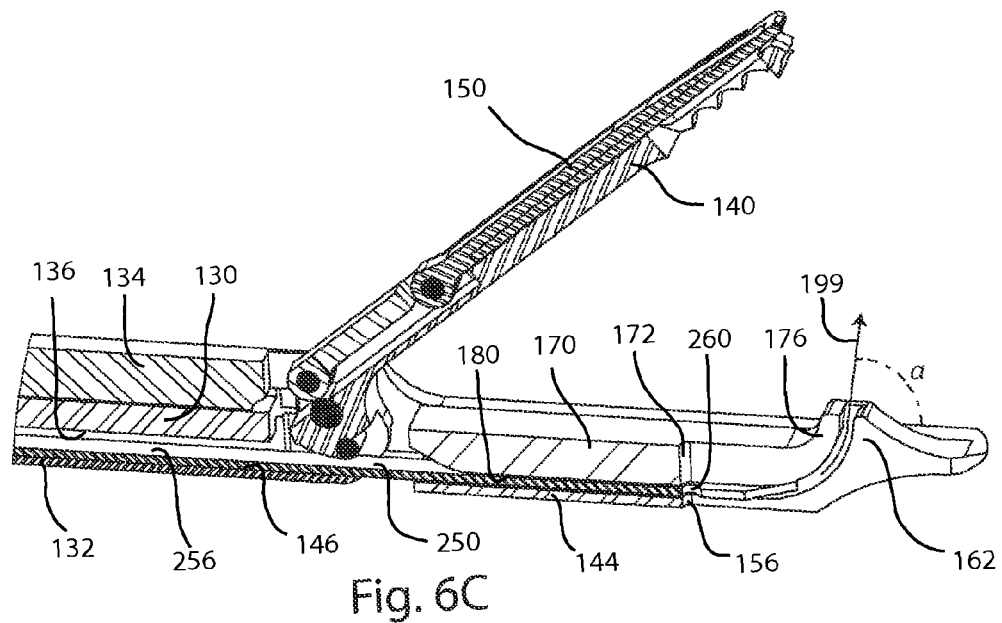

SUTURE PASSING APPARATUS AND METHOD

CROSS-REFERENCE TO RELATED APPLICATIONS

This application claims the benefit of the following:

pending U.S. Provisional Patent Application No. 61/162,601, filed Mar. 23, 2009, which is entitled SUTURE PASSING DEVICE WITH SUTURE RETRIEVAL FEATURES; and pending U.S. Provisional Patent Application No. 61/261,551, filed Nov. 16, 2009, and is entitled SUTURE PASSING DEVICE WITH SUTURE RETRIEVAL FEATURES; and pending U.S. Provisional Patent Application No. 61/261,658, filed Nov. 16, 2009, and is entitled SUTURE PASSING DEVICE WITH SUTURE RETRIEVAL FEATURES.

The above-identified documents are incorporated herein by reference.

FIELD OF THE INVENTION

This invention relates to surgical suturing devices by which suture may be passed through tissue during surgery.

BACKGROUND OF THE INVENTION

Suturing is a simple procedure when it is performed on external tissues because the needle and suture can be easily manipulated. However, in endoscopic or other minimally invasive surgical procedures that require suturing of internal tissues, access to the suturing area is limited and this limits the ability to manipulate the needle and suture. Instruments and methods for suturing remotely are especially important in these minimally invasive surgical procedures such as laparoscopic and endoscopic procedures.

Minimizing the steps and instrument manipulation required to pass a suture through an internal tissue body and reliably retrieve the suture for subsequent manipulation may result in more streamlined and reliable surgical procedures, shorter surgery duration, and improved patient outcomes. In addition, reduction of the number of access cannulas or instrument ports necessary to perform a procedure will result in decreased tissue trauma. Accordingly there is a need to minimize the number of steps, the repositioning of instruments, and the number of access points during endoscopic suturing procedures.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 6A is a perspective view of the tip portion of FIG. 1, with the upper jaw in the open position;

FIG. 6B is a perspective view of the tip portion of FIG. 1, with the upper jaw in a closed position relative to a lower jaw;

FIG. 6C is a perspective cross-sectional view of the tip portion of FIG. 6A, taken along line C-C;

DETAILED DESCRIPTION OF THE PREFERRED EMBODIMENTS

The present invention relates to surgical suturing devices and methods by which suture may be passed through tissue during surgery. Those of skill in the art will recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

The present invention provides a device for passing a portion of suture through a tissue body. The device may be operated through a single cannula or access port during a minimally invasive surgical procedure. Advantageously, the single device can accurately pass a loop of suture through the tissue, and graspingly retain the loop after passage through the tissue, allowing the suture to be pulled through the tissue and/or out of the cannula by means of a suture capturing feature, or trap, integral to the device. Thus, a separate device is not required to retrieve and/or grasp the suture after passage through the tissue. Also advantageously, the device includes a single trigger or actuation mechanism which can be actuated a single time to both move a needle to carry the suture through the tissue and operate the suture capturing feature to grasp the suture, in a phased or coordinated sequence. Further, the device can perform the steps of grasping the tissue, passing the suture through the tissue, grasping the suture, and releasing the tissue, all while remaining in the same juxtaposition relative to the tissue body. These advantages may reduce the number of steps, instruments and/or access ports necessary to place and retrieve a suture, thus reducing the duration and complexity of the procedure.

Figure 1:
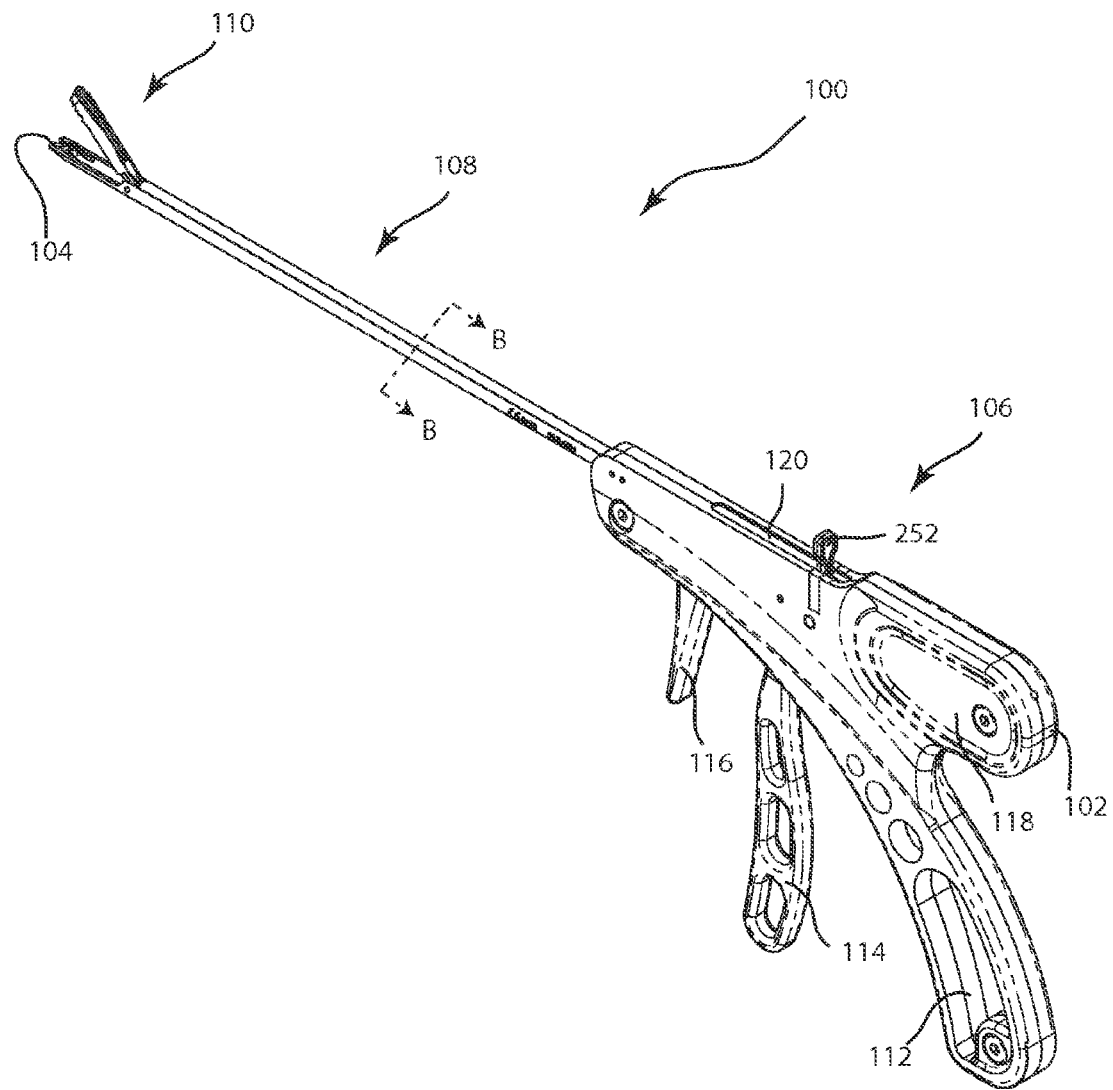
FIG. 1 is a perspective lateral view of a suture passing instrument having a handle portion, a shaft portion, a working tip portion, and a needle, with an upper jaw in an open position relative to a lower jaw.

FIG. 1 displays a perspective view of a suture passer 100. The passer 100 generally extends along a longitudinal axis from a proximal end 102 to a distal end 104, and comprises a handle portion 106, a shaft portion 108, and a tip portion 110. The terms proximal and distal, used herein, are interpreted in relative reference to the proximal and distal ends of the passer 100. Similarly, the term rearward indicates toward the proximal end, and forward indicates toward the distal end. The handle portion 106 further comprises a grip 112, a jaw actuator 114, and a combination needle/trap actuator 116, which may be shaped as a trigger. An outer housing 118 encloses a majority of the handle portion, and may be of a clamshell design comprising two or more pieces. A slot 120 provides access into the interior of the handle portion for loading and removal of needles. The majority of a removable needle 250, which extends within the handle portion and shaft portion from the slot 120 to the tip portion 110, is not visible in FIG. 1, although needle tab 252 is visible protruding from the slot 120. The handle portion and actuators may be ergonomically designed for ease of use, and may include cutouts or other features which allow for ease of cleaning, and optimizing instrument weight balancing and/or instrument weight reduction.

Figure 2A:
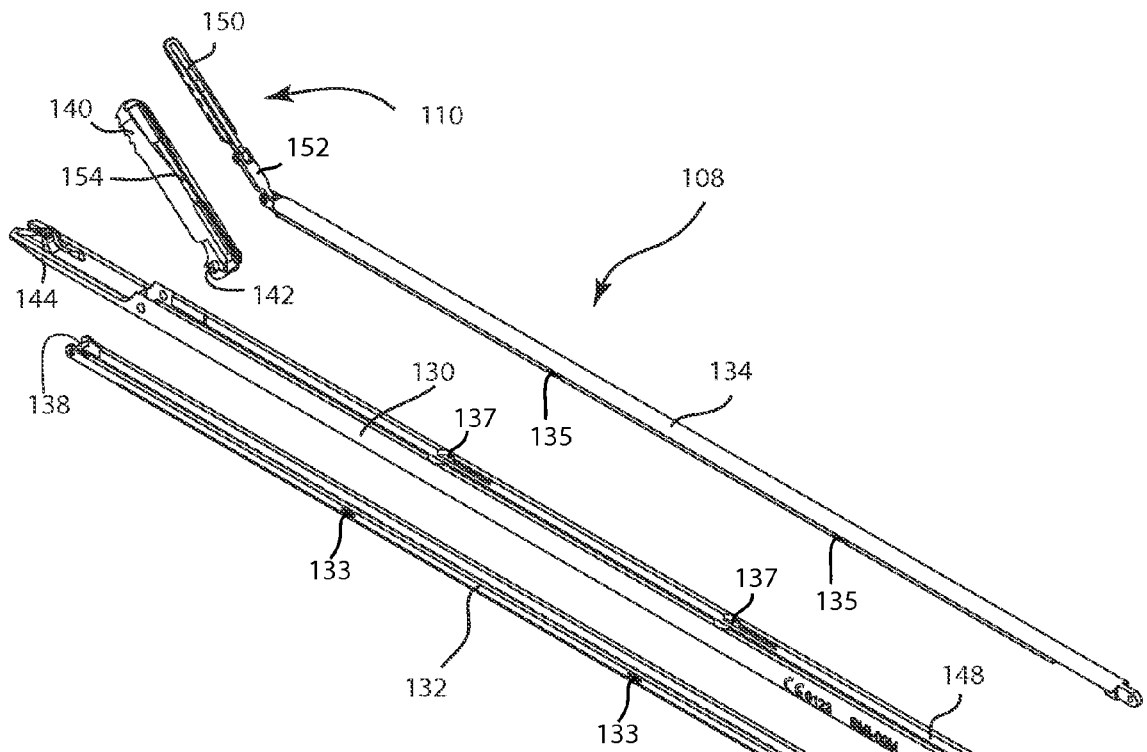
FIG. 2A is a perspective exploded view of the shaft and tip portions of the suture passing instrument of FIG. 1.
Figure 2B:
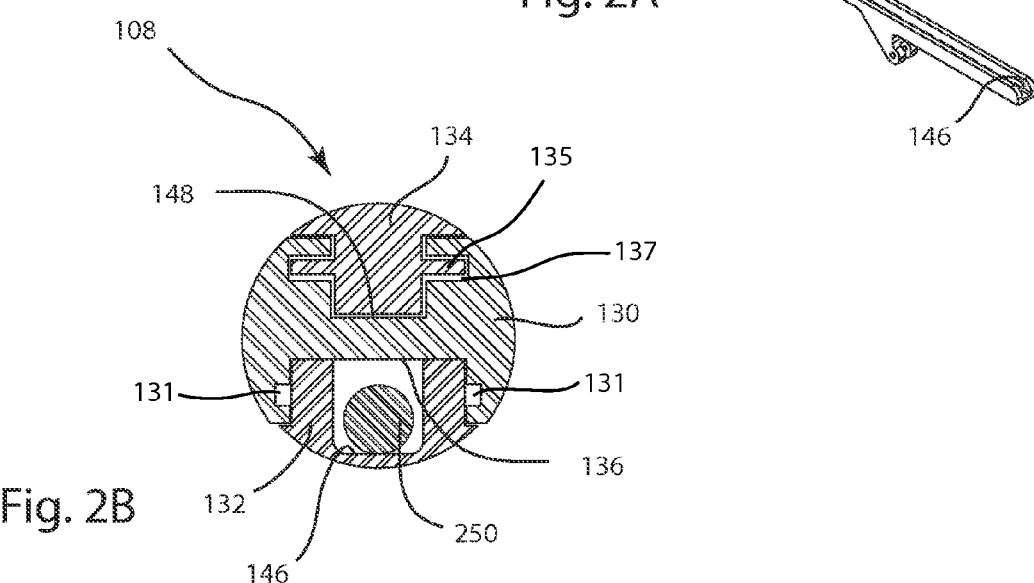
FIG. 2B is a transverse cross-sectional view of the shaft portion of FIG. 1, taken along line B-B.

FIG. 2A shows a partially exploded perspective view of the shaft 108 and tip 110 portions, while FIG. 2B shows a cross-sectional view of the shaft portion 108. Shaft portion 108 comprises three longitudinal members: a lower jaw shaft 130, an upper jaw shaft 132, and a trap door shaft 134. The lower jaw shaft 130 may be fixedly connected at its proximal end to handle portion 106, while both the upper jaw shaft 132 and the trap door shaft 134 may be independently axially translatable relative to the lower jaw shaft. At least one of the upper and lowers jaws is movable relative to the other to grasp and hold tissue between the jaws. It is appreciated that in other embodiments of the invention, either or both of the jaws may be movable relative to the other.

As seen in FIG. 2B, the lower jaw shaft 130 is substantially H-shaped when viewed in cross-section, and comprises first and second grooves 136, 148 which extend the length of the shaft, on opposite sides of the shaft. When assembled as shown in FIGS. 1 and 2B, the upper jaw shaft 132 slidably fits into the first lower jaw shaft groove 136. Upper jaw shaft 132 may include one or more tabs 133 which can slidably fit into dovetail slots 131 which are recessed into the sidewalls of the first lower jaw shaft groove 136. A linkage pin 138 connects a distal end of the upper jaw shaft 132 to an upper jaw 140. When upper jaw shaft 132 is axially translated by actuation of the jaw actuator 114, the upper jaw pivots 140 about a fulcrum pin 142, causing the upper jaw 140 to move relative to a lower jaw 144 disposed at the distal end of the lower jaw shaft 130. An upper jaw shaft groove 146 extends the length of the upper jaw shaft 132, and is sized and shaped to receive the needle 250.

The lower jaw shaft 130 further comprises the second lower jaw shaft groove 148. Trap door shaft 134 slidably fits into the groove 148, and is linked at its distal end to a trap door 150 by a trap door link 152. The trap door shaft 134 may also comprise tabs 135 which slidably engage in dovetail slots 137 recessed into the sidewalls of groove 148. The When the trap door shaft 134 is axially translated by actuation of the suturing actuator 116, the trap door 150 slides relative to the upper jaw 140, guided by a trap door track 154 on an upper surface of the upper jaw 140.

Figure 3A:
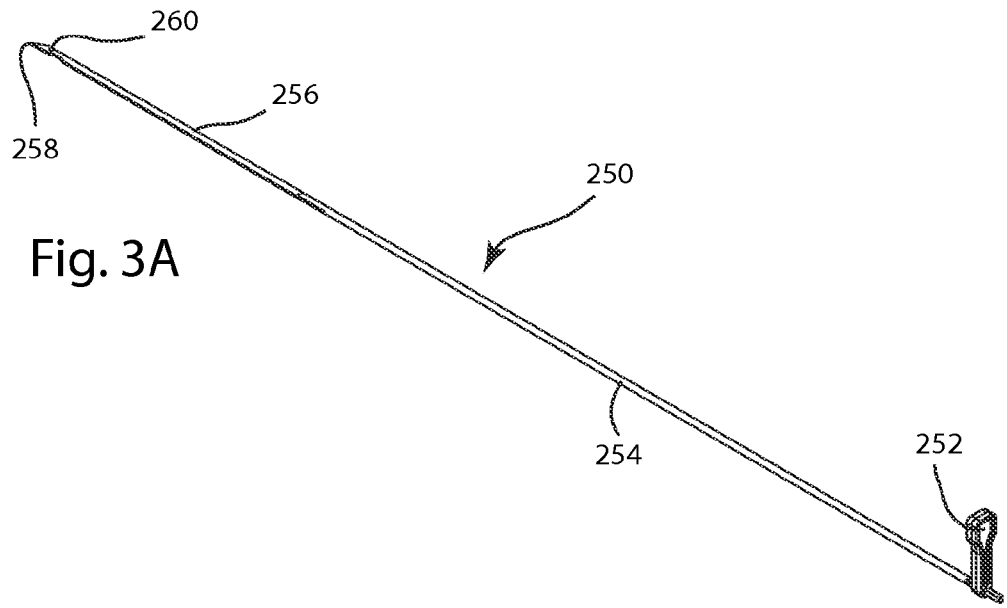
FIG. 3A is a perspective view of a needle of the suture passing instrument of FIG. 1.
Figure 3B:
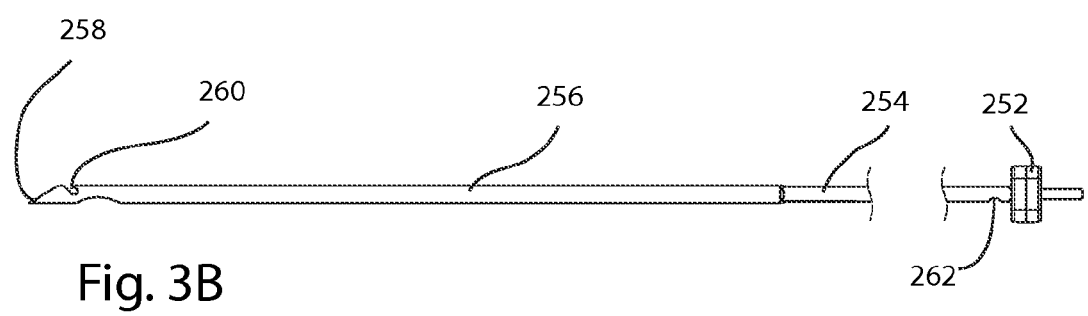
FIG. 3B is an enlarged superior view of the needle of FIG. 3A.
Figure 3C:
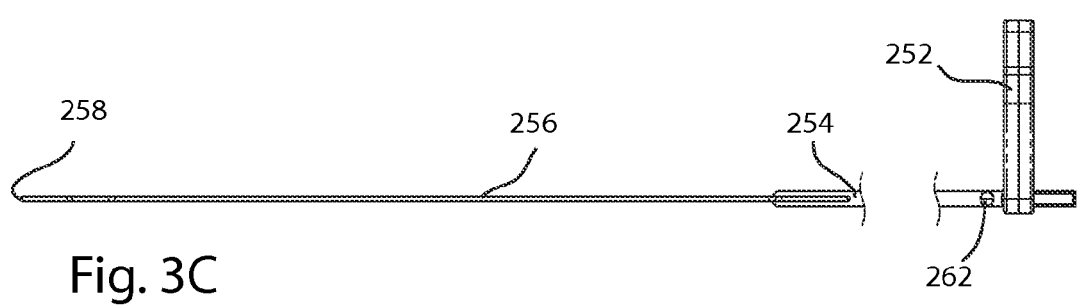
FIG. 3C is an enlarged lateral view of the needle of FIG. 3A.

FIG. 3A depicts a perspective view of an exemplary needle 250 which may be used in suture passer 100. FIG. 3B depicts a top-down view of needle 250, and FIG. 3C is a lateral view. Needle 250 may be disposable, and is removably loadable into the suture passer. Needle 250 comprises a handle, or needle tab 252 positioned at or near a first, or proximal end of the needle. The needle 250 further comprises a shaft portion 254 and a blade portion 256. A second, or distal end of the needle 250 terminates the blade portion 256 at a sharp point 258. Proximal to the point 258 on one side of the blade portion is a suture engagement feature which may be a notch 260. It is appreciated that in other embodiments of the invention, the suture engagement feature may comprise one or more notches, slots, grooves, eyes, or other features and may be disposed at a side and/or at a terminus of the needle. Near the proximal end of the needle may be an indentation or rack engagement feature 262 shaped to enable proper fitting of the needle onto a needle rack in the suture passer.

The needle blade 256 may be flat for relative ease in passing through tissues, and may comprise flexible materials such as Nitinol and other malleable metals. The proximal shaft portion 256 is generally sturdier than the blade, and may have a thicker cross section comprising a circle, rectangle or other shape. The shaft portion 256 may be somewhat flexible to aid in loading the needle into the suture passer, but is generally stiffer than the blade portion to provide support as the blade is driven through tissue. Stainless steel and/or other metals or metal alloys may comprise the shaft portion 256. The needle tab 252, shaft 254 and blade 256 may be formed monolithically or may be formed as separated pieces joined together by welds or other connecting features.

Figure 4:
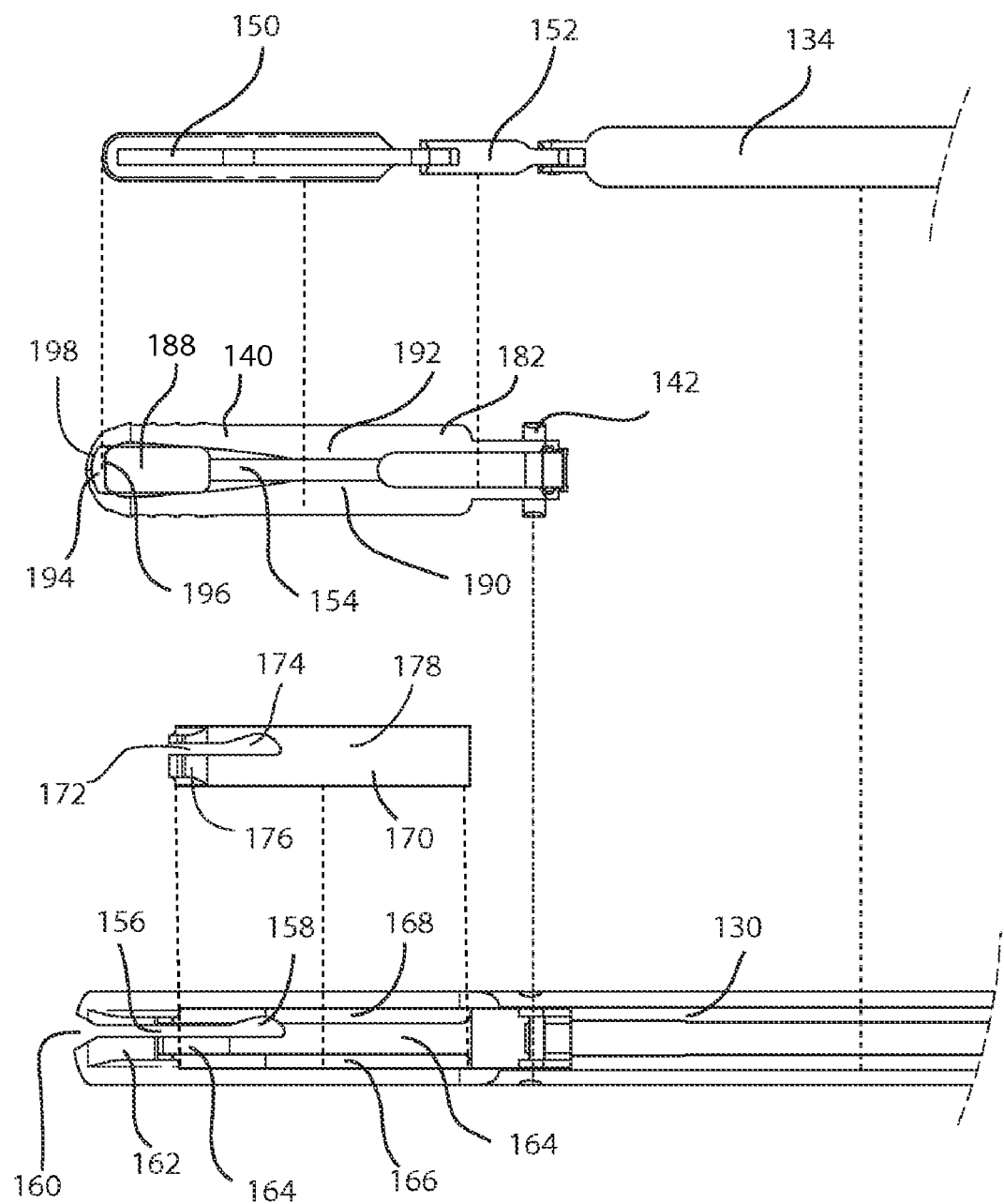
FIG. 4 is an exploded superior view of the tip portion of FIG. 1.
Figure 5:
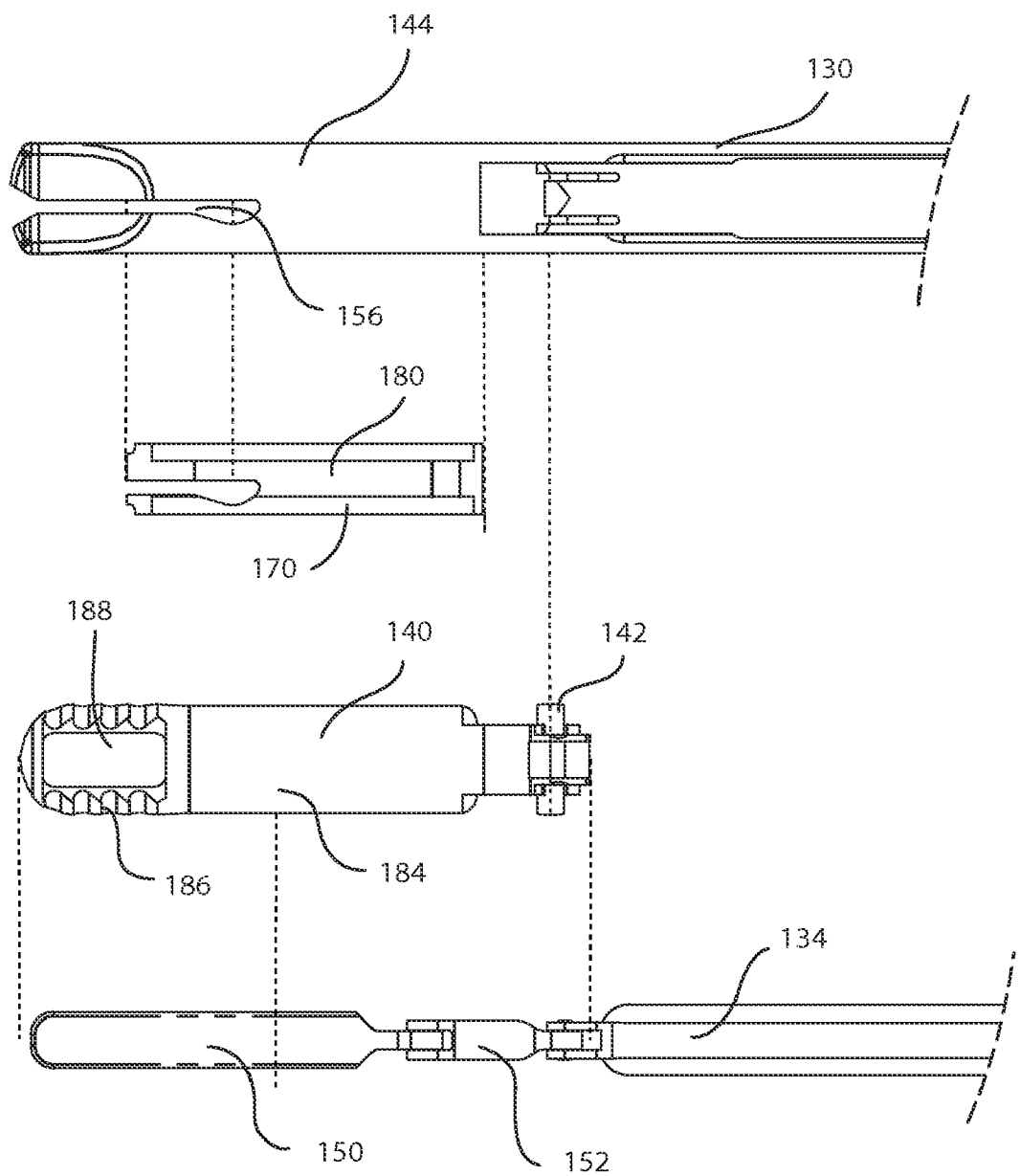
FIG. 5 is an exploded inferior view of the tip portion of FIG. 1.

The tip portion 110 of suture passer 100 is shown in more detail in FIGS. 4 and 5. FIG. 4 is an exploded top view of the tip portion 110, and FIG. 5 is an exploded bottom view of the tip portion. The lower jaw 144 is formed monolithically as an extension of lower jaw shaft 130, although in other embodiments of the invention, it could be formed as a separate piece, movable relative to the upper jaw and/or the lower jaw shaft. The fulcrum pin 142 extends transversely across the lower jaw shaft where the lower jaw 144 joins the lower jaw 130. A threading slot 156 extends longitudinally along a portion of the lower jaw 144, and may include a widened portion or alcove 158. The threading slot 156 opens at the distal end of the lower jaw 144 at a threading opening 160. A first ramp 162 is located just proximal to the distal end of the lower jaw, and slopes upward towards its proximal end. A needle track 164 extends from the proximal end of the lower jaw 144 to the first ramp 162, and curves upward where it joins the first ramp 162. Along each side of the needle track 164 are raised steps 166, 168.

A needle track cover 170 is sized and shaped to cover the needle track 164 from the proximal end of the lower jaw 144 to the first ramp 162. The needle track cover 170 includes a threading slot 172 with an alcove 174, which may precisely overlay the threading slot 156 and alcove 158 of the lower jaw 144 when the needle track cover 166 is properly fitted into the lower jaw. A second ramp 176 is formed on an upper surface 178 at the distal end of the needle track cover, and the ramp slopes up distally. When properly placed onto the lower jaw 144, the needle track cover 170 rests on the raised steps 166, 168, such that a lower surface 180 of the needle track cover 170 does not contact the needle track 164 but is raised above it, leaving space for a needle. The second ramp 176 faces the first ramp 162, leaving a gap between the first and second ramps. Together, the ramps 162, 176 may guide a needle passing between them to bend at an angle relative to the lower jaw 144. As will be seen in later figures, the needle track, ramps and gap are shaped to guide a portion of a needle as it is moved between a retracted position and an extended position.

Turning to the upper jaw 140, the upper jaw comprises an upper jaw surface 182 and a lower jaw surface 184 opposite the upper jaw surface. A plurality of teeth 186 protrude from the lower jaw surface, to aid in firmly grasping tissue between the upper and lower jaws. It is appreciated that in other embodiments of the invention, teeth or other modifications to enhance secure grasping of tissue could be included on one, both, or neither of the jaws. Such modifications may include protrusions, depressions, grooves, coatings, and roughened surfaces, among others. Extending through the upper jaw 140 from the upper jaw surface 182 to the lower jaw surface 184 is an aperture, or window 188. The trap door track 154 extends along the length of the upper jaw from its proximal end to its distal end. Along a portion of the trap door track 154, a pair of rails 190, 192 overhang the track to assist in guiding the trap door as it is moved along the track. In addition, portions of the trap door track are adjacent each lateral side of the window 188. A distal portion of the trap door track 154 comprises a lip 194, extending from a distal edge 196 of the window 188, to a distal end of the track 198. The lip 194 may be slightly recessed or stepped down from the remainder of the trap door track 154. When the trap door 150 is in a closed configuration relative to the window 188, the trap door 150 extends past the distal edge of the window 196 and overlaps at least a portion of the lip 194.

FIG. 6A depicts the tip portion 110 with the upper jaw 140 open relative to the lower jaw 144, and the trap door 150 in a closed configuration, while FIG. 6B depicts the upper jaw 140 closed relative to the lower jaw 144. It is appreciated that because the trap door 150 is hinged and actuated separately from the upper jaw 140, the trap door can remain in the same position relative to the upper jaw whether the upper jaw is open or closed. In other words, the trap door may not automatically translate relative to the upper jaw when the upper jaw is actuated to move relative to the lower jaw to grasp tissue between the jaws. Thus, the window 188 may remain open or closed independently of whether the upper jaw 140 is open or closed.

FIG. 6C is a cross-sectional view of the tip portion 110 with the upper jaw 140 open, showing detail of a pathway the needle 250 occupies when loaded into the suture passer 100. A distal portion of needle blade 256 lies in the space between needle track 164 and the lower surface 180 of the needle track cover 170, while in the shaft portion 108, a proximal portion of needle blade 256 lies between upper jaw shaft groove 146 and the lower jaw shaft groove 136. The needle notch 260 is aligned with a proximal end of threading slot 156 on the lower jaw 144, and with a proximal end of threading slot 172 on the needle track cover 170. It is appreciated that when a suture is placed in the threading slots, it may be directly threaded into the needle notch 260; it is not necessary for the needle notch 260 to "catch" the suture on the fly as the needle is moved from a retracted to an extended position. When the needle is moved to an extended configuration in which the needle distal end protrudes out between the lower jaw and the needle cover 170, the ramps 162, 176 guide the needle along a curved path defined by the lower jaw, needle cover, and ramps, as indicated by arrow 199. The needle distal end may exit the gap between the ramps at an angle α relative to the longitudinal axis of the lower jaw. In one embodiment of the invention, angle α may range from 45 to 90 degrees. In another embodiment of the invention, angle α may range from 70 to 90 degrees. In yet another embodiment, angle α may be 80 degrees.

FIGS. 7A-10B show the suture passer 100 in a series of configurations. These configurations exemplify stages which may occur when a user employs the suture passer to grasp a tissue body, pass the suture through the tissue body, and capture the suture with the passer after it has been passed through the tissue body.

Figure 7A:
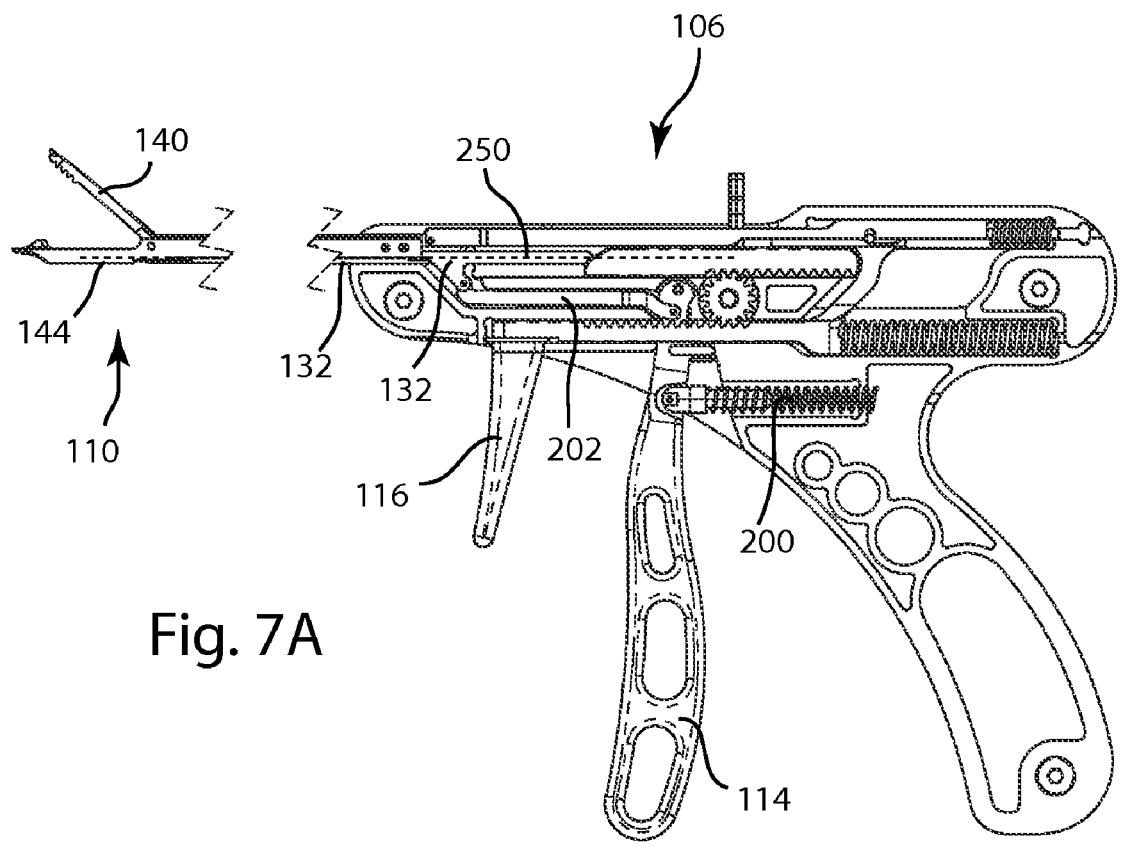
FIG. 7A is a lateral view of the suture passing instrument of FIG. 1, with the upper jaw open and a housing removed to view interior detail of the handle portion, a dashed line indicating the location of the needle shaft and blade portions.
Figure 7B:
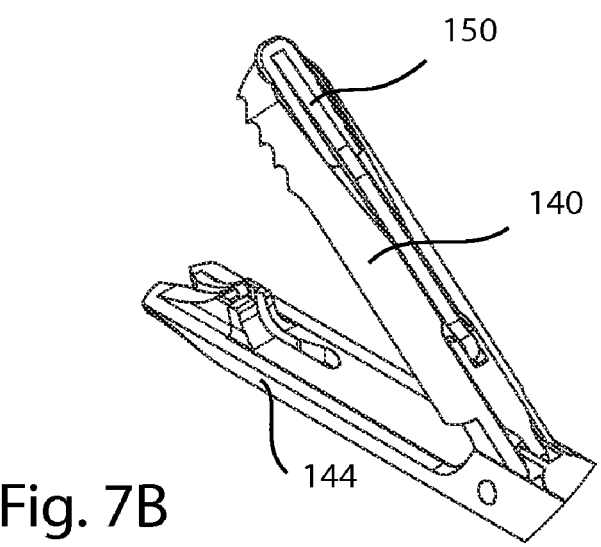
FIG. 7B is an enlarged perspective view of the tip portion of the suture passing instrument of FIG. 7A.

FIG. 7A shows a lateral view of the suture passer 100 with the upper jaw 140 in an open position relative to the lower jaw 144. The outer housing of the handle portion has been removed to see the detail within the handle portion. Jaw actuator 114 is in a forward, or open position; the actuator 114 is spring biased by a jaw spring 200 to remain in the forward position unless otherwise acted upon. A jaw actuator link 202 connects the jaw actuator 114 to the upper jaw shaft 132, so that actuation of the jaw actuator 114 controls movement of the upper jaw 140. Needle/trap actuator 116 is in a fully forward position. A dashed line indicates the position of the needle 250. FIG. 7B is an enlarged perspective view of the tip portion 110 with the upper jaw 140 in the open position, and trap door 150 in the closed configuration.

Figure 8A:
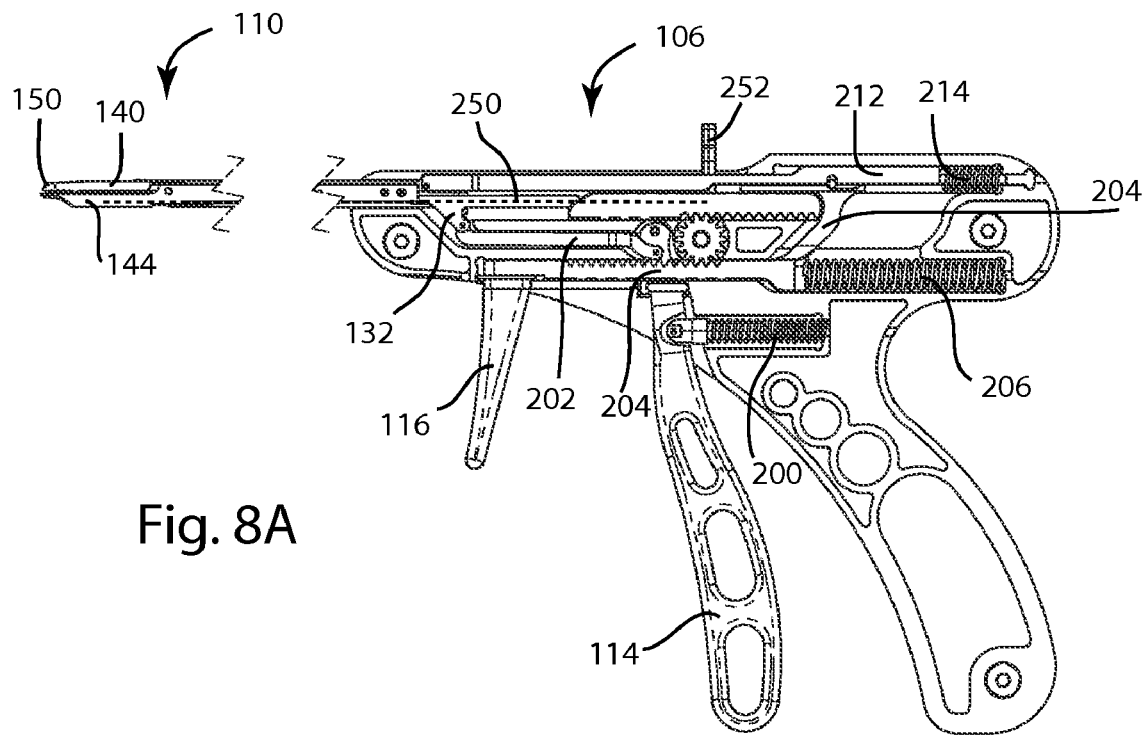
FIG. 8A is a lateral view of suture passing instrument of FIG. 7, with a jaw actuator in a proximal position and the upper jaw closed.
Figure 8B:
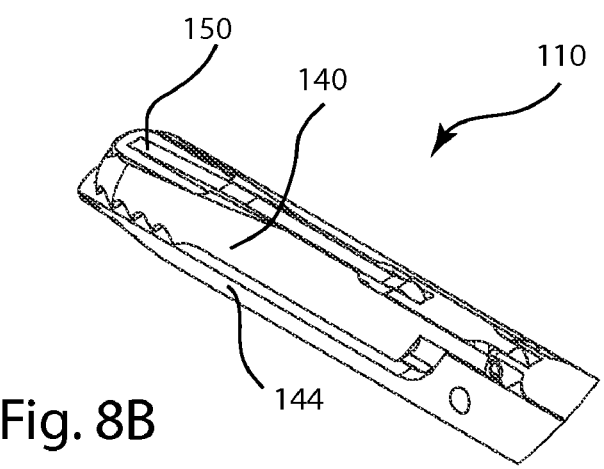
FIG. 8B is an enlarged perspective view of the tip portion of the suture passing instrument of FIG. 8A.

FIG. 8A shows a lateral view of the suture passer 100 with the upper jaw 140 in a closed position. Jaw actuator 114 is in a rearward, or closed position. Consequently, the upper jaw 140 is in a closed position relative to the lower jaw 144. Jaw actuator 114 may be held by a user in the open position, in the closed position, or in any position along a continuum in between the open and closed positions. Needle/trap actuator 116 remains in the fully forward position. A needle/trap actuator rack 204 extends rearward from the needle/trap actuator 166 and contacts a needle rack spring 206; the actuator 116 is spring biased by the needle rack spring 206 to remain in the forward position unless otherwise acted upon. The needle/trap actuator 116 is further linked to a trap door linkage 212 which abuts a trap door spring 214. The trap door spring 214 is not compressed and the trap door 150 is in the closed configuration relative to the upper jaw. FIG. 8B is an enlarged perspective view of the tip portion 110 with the upper jaw 140 in the closed position, and trap door 150 in the closed configuration.

Figure 9A:
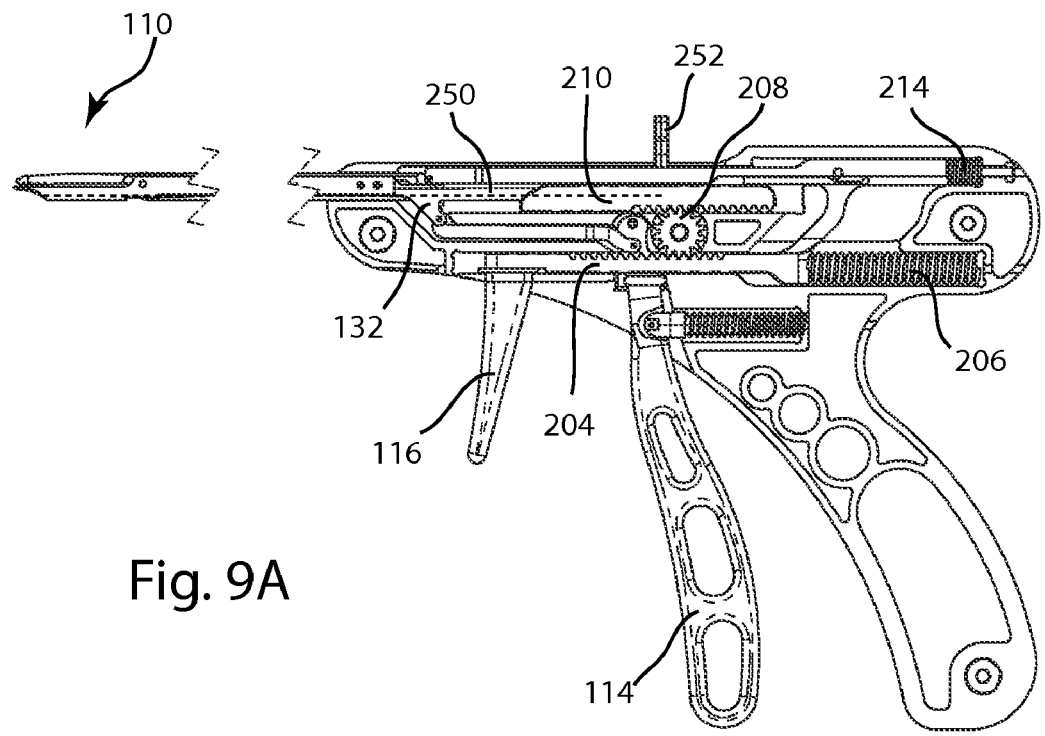
FIG. 9A is a lateral view of suture passing instrument of FIG. 7, with a needle/trap actuator in a partially proximal position and a capture feature on the upper jaw in an open configuration.
Figure 9B:
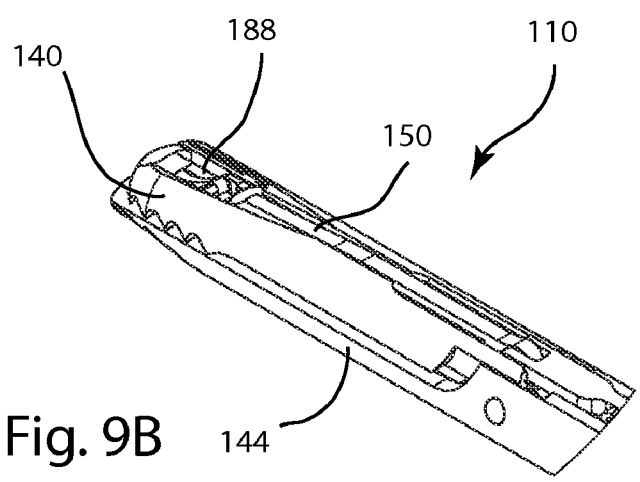
FIG. 9B is an enlarged perspective view of the tip portion of the suture passing instrument of FIG. 9A.

FIG. 9A shows a lateral view of the suture passer 100 with the upper jaw 140 in the closed position and the trap door 150 in an open configuration. FIG. 9B is a perspective view of the tip portion 110, in the same configuration. Needle/trap actuator 116 is in a partially actuated or partial rearward position. Trap door spring 214 is compressed, and trap door 150 is in an open position relative to the window 188 in the upper jaw 140, as can be seen in FIG. 9B. The needle/trap actuator rack 204 extends rearward from the needle/trap actuator 166 and contacts a needle rack spring 206, which is partially compressed. The needle/trap actuator rack 204 is in meshed engagement with a needle pinion gear 208, which is also in meshed engagement with a needle rack 210. A dashed line indicates the position of the needle 250 in the needle rack 210 and upper jaw shaft 132. As needle/trap actuator 116 is pulled rearward, needle pinion gear 208 rolls forward along needle/trap actuator rack 204 and causes needle rack 210 to move forward. As needle rack 210 moves forward, needle 250 is carried forward, slidably translating in the upper jaw shaft groove 146 of upper jaw shaft 132. In this view, it is noted that the needle has been moved slightly forward; this is evidenced by the partially advanced position of needle tab 252. However, the needle is not in a fully extended position, and the needle tip does not protrude through the window 188.

In certain embodiments of the invention, needle/trap actuator 116, needle/trap actuator rack 204, and needle pinion gear 208 may be characterized as an actuation mechanism. The needle 250 may be connected to the actuation mechanism by a first linkage comprising needle rack 210. A separate second linkage comprising trap door link 152, trap door shaft 134 and trap door linkage 212 may connect the capture feature, or trap door 150, to the actuation mechanism.

Figure 10A:
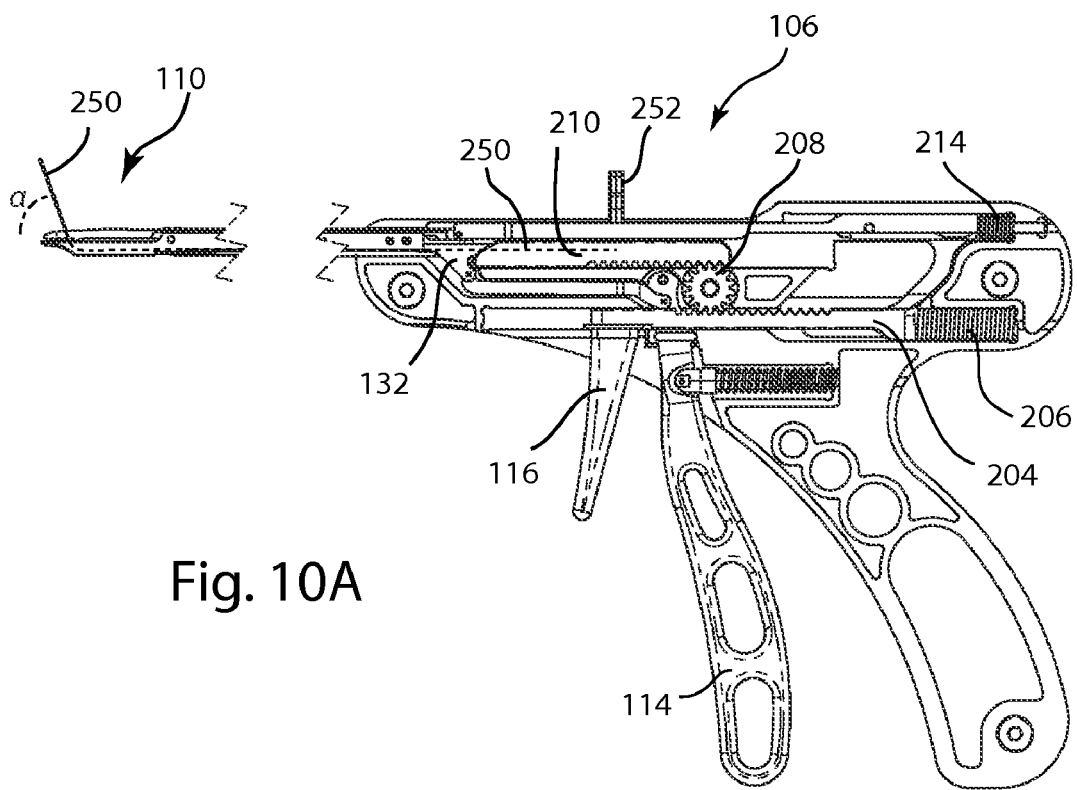
FIG. 10A is a lateral view of suture passing instrument of FIG. 7, with the needle/trap actuator in a fully proximal position, the capture feature open, and a needle extending through an upper jaw window.
Figure 10B:
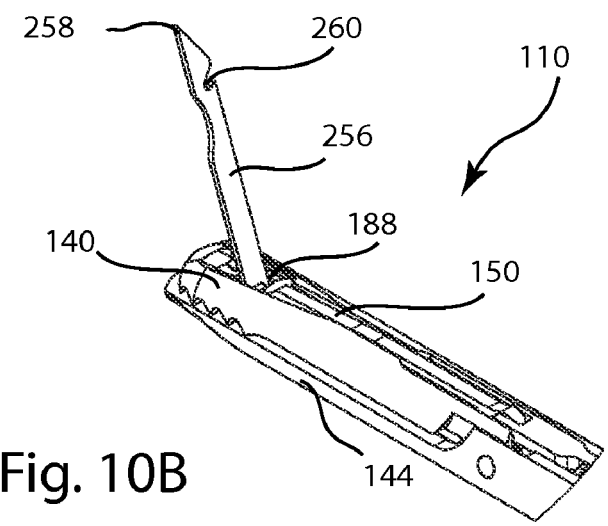
FIG. 10B is an enlarged perspective view of the tip portion of the suture passing instrument of FIG. 10A.

FIG. 10A shows a lateral view of the suture passer 100 with the upper jaw 140 in the closed position, the trap door 150 in an open configuration, and a portion of the needle blade 256 protruding through the open window 188. FIG. 10B is an enlarged perspective view of the tip portion 110 in the same configuration. Needle/trap actuator 116 is in a fully rearward position, and needle rack spring 206 is fully compressed. The needle rack 210 has been moved completely forward, as evidenced by the advanced position of the needle tab 252. A distal portion of the needle, comprising the needle tip 258 and suture engaging notch 260 protrudes through the window 188 at angle α relative to the lower jaw 144. In this embodiment, angle α is about 80 degrees, or nearly perpendicular.

Referring to FIGS. 7A-10B, it is appreciated that a single actuation of the needle/trap actuator 116, can urge the suture passer through all the stages depicted in the figures. A single actuation may be characterized as pulling and then releasing the needle/trap actuator 116. In a resting state, needle/trap actuator is biased forward by needle rack spring 206, providing the trap door 150 in a closed configuration and the needle in a rearward or retracted position, as in FIGS. 7A and 7B, and FIGS. 8A and 8B. Needle/trap actuator 116 may be actuated by pulling proximally on the actuator 116 like a trigger, whereby, in a coordinated sequence, trap door 150 is slid proximally to an open configuration (FIGS. 9A and 9B), and then needle 250 is moved to an extended position in which it extends through the window 188 (FIGS. 10A and 10B). The needle/trap actuator 116 may then be released, or allowed to move distally wherein the needle is retracted back through the window 188 (FIGS. 9A and 9B), and then the trap door is slid distally to return to the closed configuration (FIGS. 8A and 8B). Needle/trap actuator 116 may be released in a controlled manner in which the operator maintains hand pressure on the actuator 116 as it moves distally, or the actuator 116 may be released and allowed to move distally without hand pressure from the operator.

An alternative embodiment of the invention may comprise independent actuation mechanisms for moving the needle and moving the trap door. A first actuator may be linked to the needle and actuable to move the needle between the retracted and extended positions, and a separate second actuator may be linked to the trap door to move the trap door relative to the window to provide the open and closed configurations. It is appreciated that in this embodiment, the trap door may remain in the open configuration relative to the window, regardless of the position of the needle. In this and other embodiments, a locking mechanism may be included wherein the trap door may be locked in the open position.

FIGS. 11A through 13 illustrate a method of using suture passer 100 to pass a suture through a tissue body. The tissue body may be any tissue including but not limited to: tendon, muscle, cartilage, ligament, peritoneum, and other soft tissues. A tissue body may comprise a single strand, layer or piece; or multiple strands, layers or pieces; and may comprise a combination of tissues such as muscle and tendon.

Figure 11A:
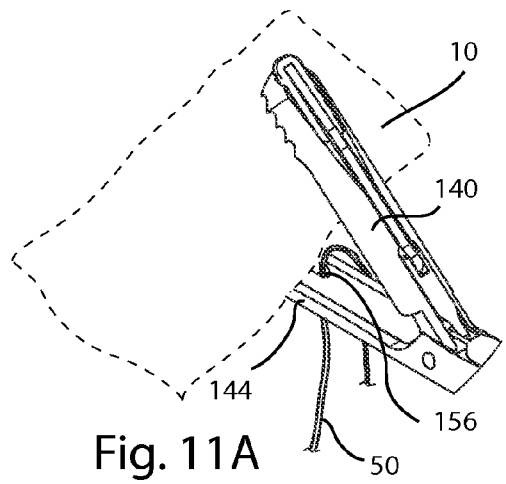
FIG. 11A is a perspective view of the tip portion of the suture passing instrument of FIG. 1, with the upper jaw in the open position, a tissue body overlaying the lower jaw, and a suture threaded into the needle.
Figure 11B:
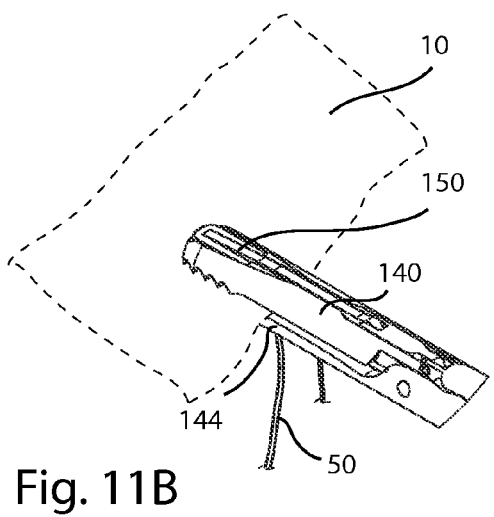
FIG. 11B is a perspective view of the tip portion and tissue body of FIG. 11A, with the upper jaw closed to grasp the tissue body between the upper and lower jaws.

Referring to FIG. 11A, a tissue body 10 is shown with the tip portion 110 of suture passer 100 juxtaposed adjacent to the tissue body such that a portion of the tissue body is positioned between the open upper jaw 140 and the lower jaw 144. A suture 50 has been positioned to pass through the threading slot 156 of the lower jaw and is threaded in the notch 260 of the needle 250, which is lined up with the threading slot. It is appreciated that the suture may be directly threaded into the needle notch 260. In FIG. 11B, also with reference to FIG. 8A, the upper jaw has been pivoted relative to the lower jaw by actuation of jaw actuator 114 to grasp the tissue body 10 between the jaws.

Figure 11C:
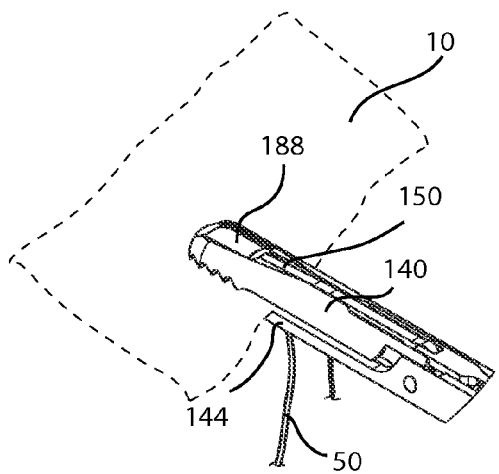
FIG. 11C is a perspective view of the tip portion and tissue body of FIG. 11A, with the capture feature on the upper jaw in an open configuration.

Referring to FIGS. 11C and 9A, the trap door 150 has been actuated to a first, or open configuration relative to the upper jaw 140, by actuation of needle/trap actuator 116. A portion of the tissue body 10 can be seen through open window 188, since the tissue body 10 overlays the lower jaw 144.

Figure 11D:
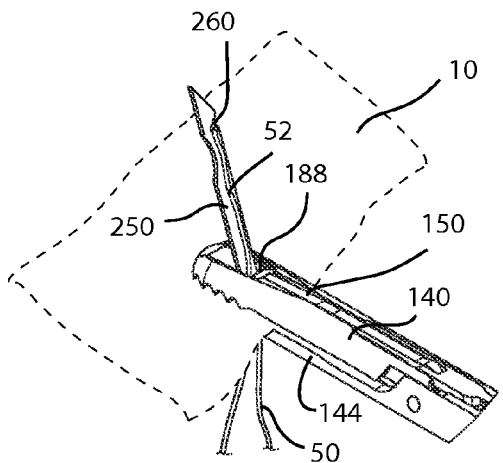
FIG. 11D is a perspective view of the tip portion and tissue body of FIG. 11A, with the needle protruding through the tissue body and the upper jaw window, and a suture carried through the tissue body and the upper jaw window in a needle notch.

Referring to FIGS. 11D and 10A, the needle 250 has been moved from a retracted position to an extended position whereby it has pierced through the tissue body 10 and protrudes out through the window 188. The suture 50, threaded in the needle notch 260, has been carried by the needle 250 through the tissue body 10 and the window 188. By having been drawn up by the needle 250, a portion of the suture 50 is in the form of a loop 52.

Figure 12A:
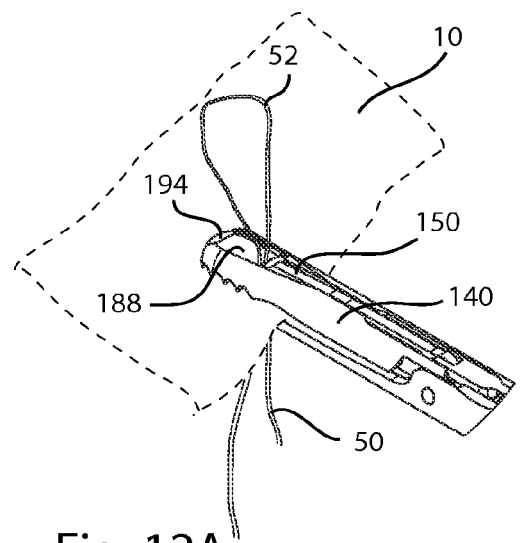
FIG. 12A is a perspective view of the tip portion and tissue body of FIG. 11A, with the needle retracted and a suture loop extending through the upper jaw window.

Referring to FIGS. 12A and 9A, needle/trap actuator 116 has been released and the needle 250 has been moved back to the retracted position. Loop 52 remains extended through the window 188, and may be in a relatively vertical or transverse orientation with respect to the upper jaw 140, as seen in FIG. 12A. The trap door 150 remains in the open configuration, for needle/trap actuator 116 has not yet moved sufficiently proximally, or rearward, to cause the trap door 150 to shut.

Figure 12B:
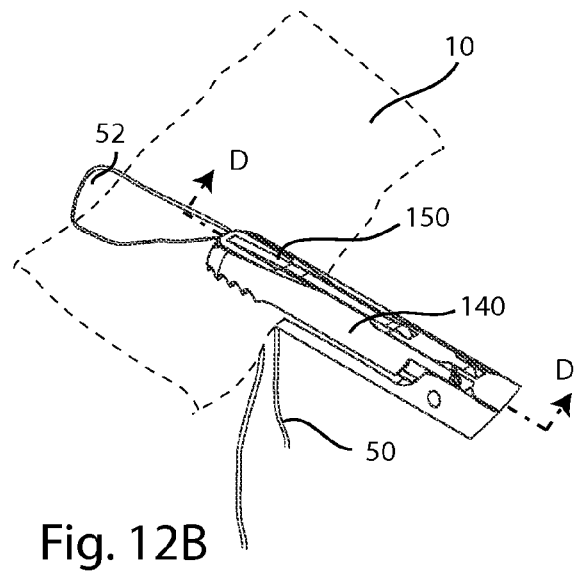
FIG. 12B is a perspective view of the tip portion and tissue body of FIG. 11A, with the capture feature in a closed configuration, trapping the suture loop between the capture feature and the upper jaw.

Referring to FIGS. 12B and 8A, needle/trap actuator 116 is in the fully forward or distal position, and trap door 150 is in the closed configuration relative to the upper jaw 140. Suture 50 is firmly gripped between the trap door 150 and the upper jaw 140. As will be seen in detail in a later figure, suture 50 is folded, or bent, around a corner on the upper jaw and is sandwiched between the lower surface of the trap door and the lip 194 on the upper jaw 140. The overlap between the trap door and the lip allows a greater surface area of suture to be trapped, or sandwiched, between the bottom of the trap door and the lip than would be, for example, pinched between the distal edge of the trap door and a side of the window. Due to the folding of the suture around the lip corner, loop 52 is in a relatively horizontal or aligned orientation with respect to upper jaw 140.

Figure 12C:
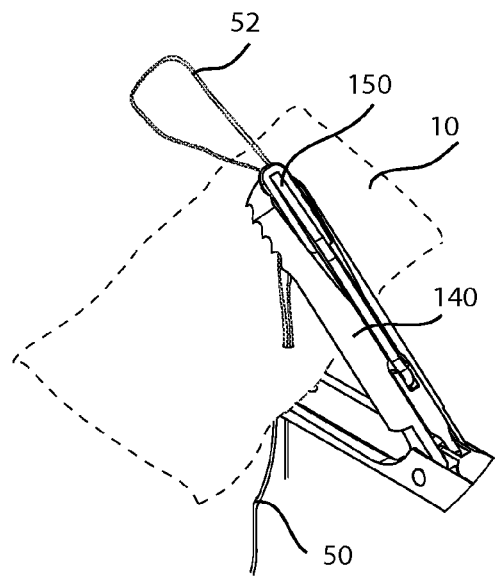
FIG. 12C is a perspective view of the tip portion and tissue body of FIG. 11A, with the upper jaw open and the suture partially pulled through the tissue body.
Figure 12D:
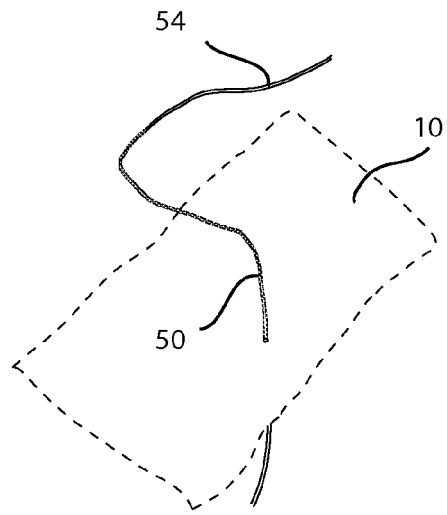
FIG. 12D is a perspective view of the tissue body of FIG. 11A, with the suture passed through the suture body such that a free end of the suture has been moved free of the tissue body.

In FIG. 12C, the upper jaw 140 has been opened relative to the lower jaw 144 and the tissue body 10 is released. At this juncture, the suture passer 100 may be moved relative to the tissue body, with the suture still firmly gripped between the trap door 150 and the upper jaw 140, to pull a portion of suture through the tissue body. As seen in FIG. 12D, the suture 50 may be pulled through the tissue body until a free end 54 of the suture is pulled entirely though the tissue body, if desired. Once the suture is at the desired location, needle/trap actuator 116 may be partially actuated or pulled proximally, far enough to open the trap door 150 and release the suture 50.

Figure 13:
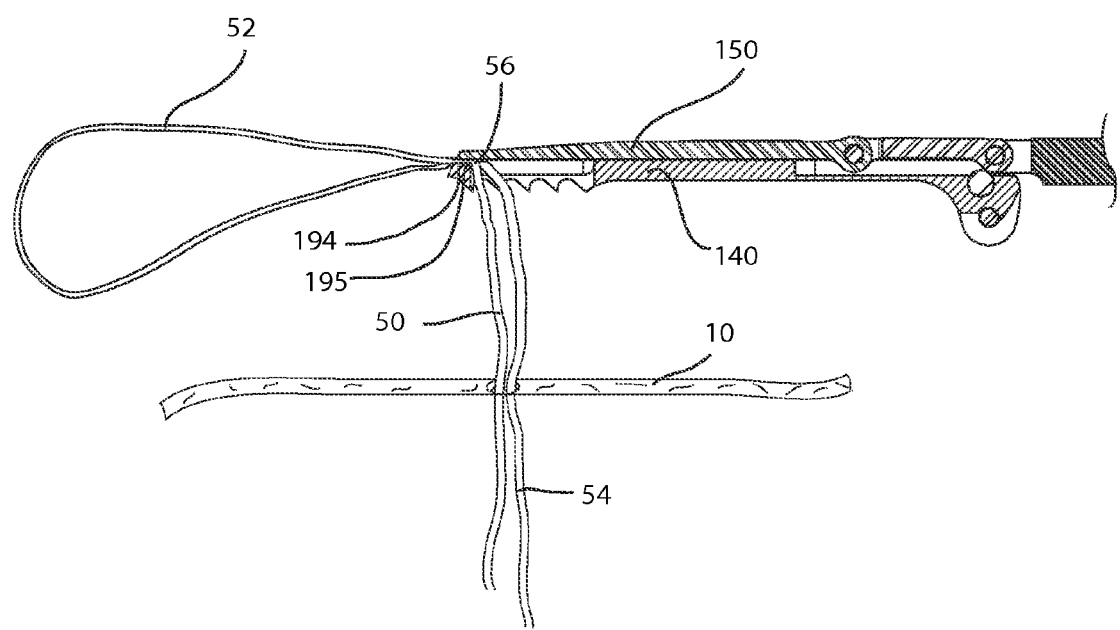
FIG. 13 is an enlarged cross-sectional view of the tip portion of FIG. 12B, taken along line D-D, showing the suture bent around a corner of the upper jaw.

Referring to FIG. 13, a lateral cross-sectional view of the suture passer tip portion 110 minus the lower jaw is shown, with a suture 50 trapped between the trap door 150 and the lip 194 of the upper jaw 140. Suture 50 is folded, or bent around a corner 195 at a proximal or interior edge of the lip 194. At the point where the suture 50 is bent around the corner, a suture bend 56 is formed. Corner 195 and bend 56 may each form an angle ranging from 20 to 70 degrees. More specifically, corner 195 and bend 56 may each form an angle of 45 degrees.

In one method of use, a suture may be attached to a suture anchor which is anchored in a bone. Suture passer 100 may be employed as described previously to pass a portion of the suture through a tissue body, whereafter the suture may be knotted or tied to fasten the tissue body to the bone. In another method of use, the suture may be attached to a suture anchor which is anchored in a bone, leaving two free suture ends. Using suture passer 100 two times successively, each free end may be passed through a tissue body, and the free ends knotted together to tie the tissue body firmly to the bone. In yet another alternative, two free ends of a suture may be passed through two separate tissue bodies, and the free ends tied or knotted together to join the tissue bodies together.

Suture passer 100 may be used independently, or in conjunction with other tools and/or cannulas to perform a surgical procedure. An access cannula may be positioned to provide access to a surgical site, and tip 110 and shaft 108 portions passed into the cannula. Tip portion 110 may protrude from the cannula at the surgical site and be actuated to pass a suture through a tissue body at the surgical site. It is appreciated that the upper jaw may be actuated relative to the lower jaw to grasp, move and release tissue independently of being actuated to pass a suture through a tissue. It is also appreciated that the jaws may grasp a tissue body, then release and regrasp the tissue body to adjust the position of the window relative to the tissue body, prior to passing a suture through the tissue body. After passage of the suture through a tissue body and grasping of the suture with the trap door capture feature, a portion or end of the suture may be retrieved out of the cannula by withdrawing the shaft and tip portions from the cannula, with the suture still firmly grasped between the trap door and the lip.

The present invention may be embodied in other specific forms without departing from its spirit or essential characteristics. It is appreciated that various features of the above-described examples can be mixed and matched to form a variety of other alternatives. It is also appreciated that this system should not be limited to passing a suture through a tendon or ligament; it may be used to pass a suture through any soft tissues. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A suturing apparatus for passing suture through a tissue body, comprising:
  a first jaw member disposed at a distal end of the suturing apparatus, the first jaw member having an aperture extending therethrough;
  a needle having a suture engagement feature, the needle movable between a retracted position and an extended position relative to the distal end of the suturing apparatus, wherein in the extended position a portion of the needle extends through the aperture to carry a portion of suture through the aperture; and
  a capture feature formed on the distal end of the suturing apparatus, the capture feature actuable to releasably grip and retain suture;
  wherein the suturing apparatus is actuable by a single actuation of an mechanism, while remaining in an unmoved juxtaposition relative to the tissue body, to move the needle from the retracted position to the extended position to carry the portion of suture through the tissue body and the aperture, and to actuate the capture feature to firmly and releasably grip the portion of suture after the portion of suture has been carried by the needle through the tissue body and the aperture.

2. The suturing apparatus of claim 1, further comprising:
  a first linkage connecting the needle to the actuation mechanism; and
  a second linkage connecting the capture feature to the actuation mechanism, the first and second linkages separate from one another.

3. The suturing apparatus of claim 1, further comprising:
  a handle portion disposed at a proximal end of the suturing apparatus, wherein the actuation mechanism is located on the handle portion.

4. The suturing apparatus of claim 1, wherein the capture feature comprises a trap door disposed immediately adjacent the aperture, wherein the trap door is actuable between a first position and a second position relative to the aperture to transform the aperture from an open configuration for passage of suture therethrough, to a closed configuration for gripping of suture between the trap door and the first jaw member.

5. The suturing apparatus of claim 4, wherein the trap door is slidable along the first jaw member from a proximal position to a distal position relative to the first jaw member to transform the aperture from the open configuration to the closed configuration.

6. The suturing apparatus of claim 1, further comprising a second jaw member disposed at the distal end of the suturing apparatus, wherein at least one of the first and second jaw members is movable relative to the other to grasp tissue between the jaw members.

7. A method for passing suture through a tissue body, comprising:
  positioning an aperture of a first jaw member of a suturing apparatus adjacent a tissue body to be sutured, the first jaw member disposed on a distal end of the suturing apparatus;
  moving a needle of the suturing apparatus from a retracted position to an extended position relative to the distal end of the suturing apparatus, the needle moving through the tissue body and the aperture and carrying a portion of a suture through the tissue body and through the aperture, actuating a capture feature formed on a distal end of the suturing apparatus; and gripping the suture portion with the capture feature after the suture portion has been carried through the tissue body and the aperture.

8. The method of claim 7, further comprising moving the needle from the extended position to the retracted position after carrying the portion of the suture through the tissue body and through the aperture.

9. The method of claim 7, further comprising moving the needle from the extended position to the retracted position before gripping the suture with the capture feature.

10. The method of claim 7, further comprising actuating the capture feature to release the suture portion after gripping the suture portion with the capture feature.

11. The method of claim 7, further comprising moving at least one of the first jaw member and a second jaw member disposed at the distal end of the suturing apparatus, to grasp the tissue body between the jaw members.

12. The method of claim 7, wherein the suturing apparatus further comprises an actuation mechanism, the method further comprising actuating the actuation mechanism a single time to both move the needle and actuate the capture feature.

13. The method of claim 12, wherein movement of the needle and actuation of the capture feature occur in a coordinated sequence upon the single actuation of the actuation mechanism.

14. The method of claim 7, wherein the capture feature comprises a trap door disposed immediately adjacent the aperture, wherein actuating the capture feature comprises moving the trap door between a first position and a second position relative to the aperture thereby transforming the aperture from an open configuration to a closed configuration.

15. The method of claim 14 wherein moving the trap door comprises sliding the trap door distally along the first jaw member to transform the aperture from the open configuration to the closed configuration.

16. The method of claim 14, wherein gripping the suture portion with the capture feature comprises clamping the suture portion between the trap door and the first jaw member.

17. A suturing apparatus for passing suture through a tissue body, comprising:

first and second jaw members disposed at a distal end of the suturing apparatus, at least one of the first and second jaw members movable relative to the other to grasp tissue between the jaw members, the first jaw member comprising a window extending therethrough;

a needle having a suture engagement feature, the needle movable between a retracted position and an extended position relative to the distal end of the suturing apparatus, wherein, in the extended position, a portion of the needle extends through the window to carry a portion of suture through the window;

a trap door disposed immediately adjacent the window, the trap door movable relative to the window to provide an open configuration and a closed configuration, wherein when in the closed configuration, a portion of suture extending through the window is captured between the trap door and the first jaw member; and a first actuation mechanism actuable by a single actuation to move the needle between the retracted and extended positions, and to move the trap door relative to the window to provide the open and closed configurations, in a coordinated sequence.

18. The suturing apparatus of claim 17, wherein when a portion of suture is positioned between the trap door and the first jaw member in the closed configuration, the portion of suture is bent around a corner.

19. The suturing apparatus of claim 18, wherein a distal edge of the window comprises the corner.

20. The suturing apparatus of claim 17, wherein the trap door is axially movable from a first position in which a distal edge of the trap door is spaced apart from a distal edge of the window to provide the open configuration, to a second position in which the distal edge of the trap door overlaps the distal edge of the window to provide the closed configuration.

21. The suturing apparatus of claim 17, wherein the trap door is permanently in the open configuration relative to the window.

22. The suturing apparatus of claim 17, further comprising a second actuation mechanism, wherein the first actuation mechanism is actuable to move the needle between the retracted and extended positions, and the second actuation mechanism is actuable to move the trap door relative to the window to provide the open and closed configurations.

23. A method for passing suture through a tissue body, comprising:

positioning first and second jaw members disposed at a distal end of a suturing apparatus relative to a tissue body such that a window extending through the first jaw member overlays the tissue body;

moving one of the first and second jaw members relative to the other to grasp the tissue body between the jaw members; and actuating a first actuation mechanism with a single actuation, wherein actuating the first actuation mechanism comprises, in a coordinated sequence:

moving a trap door disposed immediately adjacent the window relative to the window to provide an open configuration;

moving a needle having a suture engagement feature from a retracted position to an extended position relative to the distal end of the suturing apparatus;

moving a portion of the needle through the tissue body and the window thereby carrying a portion of suture through the tissue body and the window;

moving the needle from the extended position to the retracted position thereby moving the portion of the needle out of the window and leaving the portion of suture extending though the tissue body and the window; and moving the trap door relative to the window to provide a closed configuration, thereby capturing the portion of suture between the trap door and the first jaw member.

24. The method of claim 23, wherein capturing the portion of suture between the trap door and the first jaw member in the closed configuration further comprises bending the portion of suture around a corner.

25. The method of claim 24, wherein a distal edge of the window comprises the corner.

26. The method of claim 23, further comprising moving one of the first and second jaw members relative to the other to release the tissue body from between the jaw members.

27. The method of claim 26, further comprising repositioning the suturing apparatus relative to the tissue body after the portion of suture is captured between the trap door and the first jaw member to pass additional suture through the tissue body.

28. The method of claim 23, wherein moving the trap door relative to the window to provide the open configuration comprises axially translating the trap door along the window to a first position in which a distal edge of the trap door is spaced apart from a distal edge of the window to provide the open configuration, and wherein moving the trap door relative to the window to provide the closed configuration comprises axially translating the trap door along the window to a second position in which the distal edge of the trap door overlaps the distal edge of the window.

29. The method of claim 23, further comprising threading the suture into the suture engagement feature while the needle is in the retracted position.

30. The method of claim 23, further comprising actuating the first actuation mechanism to move the needle between the retracted and extended positions, and actuating a second actuation mechanism independent of the first actuation mechanism to move the trap door relative to the window to provide the open and closed configurations.

* * * * *